United States Patent [19]

Huth et al.

[11] 4,153,713
[45] May 8, 1979

[54] 4-(POLYALKOXYPHENYL)-2-PYRROLIDONES (II)

[75] Inventors: Andreas Huth; Ralph Schmiechen; Wolfgang Kehr; Dieter Palenschat; Gert Paschelke; Helmut Wachtel, all of Berlin, Fed. Rep. of Germany

[73] Assignee: Schering Aktiengesellschaft, Berlin and Bergkamen, Fed. Rep. of Germany

[21] Appl. No.: 724,213

[22] Filed: Sep. 17, 1976

[30] Foreign Application Priority Data

Sep. 18, 1975 [DE] Fed. Rep. of Germany ....... 2541855

[51] Int. Cl.$^2$ ..................... A61K 31/40; C07D 207/26
[52] U.S. Cl. ..................................... 424/274; 546/208; 546/187; 260/326.25; 260/326.34; 260/326.4; 260/244.4; 544/142; 544/372; 424/248.54; 424/248.55; 424/250; 424/267
[58] Field of Search ....................... 260/326.4, 326.34; 424/274

[56] References Cited

U.S. PATENT DOCUMENTS

| | | | |
|---|---|---|---|
| 2,975,193 | 3/1961 | Dice et al. | 260/326.5 M |
| 3,644,398 | 2/1972 | Helsley | 260/326.4 |
| 3,644,414 | 2/1977 | Helsley | 260/326.4 |
| 3,956,314 | 5/1976 | Strubbe et al. | 260/326.5 FL |
| 4,012,495 | 3/1977 | Schmiechen et al. | 260/326.45 |

FOREIGN PATENT DOCUMENTS

| | | | |
|---|---|---|---|
| 709405 | 5/1965 | Canada | 260/326.5 M |
| 49-16870 | 1974 | Japan | 260/326.5 |
| 1140188 | 1967 | United Kingdom | 260/326.5 |

OTHER PUBLICATIONS

Hackh's Chemical Dictionary, p. 33.
The Condensed Chemical Dictionary, p. 41.
Francois Debarre et al., Chem. Abs., vol. 70: 106372h (1969) (abstract of British Pat. No. 1,140,188).
Belostotskaya et al., Chem. Abs., vol. 65: 5431f (1966).
Rothe et al., Chem. Abs., vol. 66: 55737p (1967).

*Primary Examiner*—Donald G. Daus
*Assistant Examiner*—Mary C. Lee
*Attorney, Agent, or Firm*—Millen & White

[57] ABSTRACT

4-(Polyalkoxyphenyl)-2-pyrrolidones of the formula

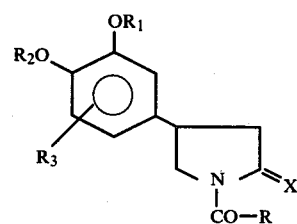

wherein $R_1$ and $R_2$ are hydrocarbon;
$R_3$ is hydrogen or methoxy;
R is O-alkyl, O-aryl, O-aralkyl, $NH_2$, NH-alkyl, NH-aryl, NH-aralkyl, N(alkyl)$_2$, N(aryl)$_2$ or

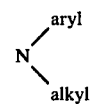

and X is O or S, are neuropsychotropic agents.

17 Claims, No Drawings

4-(POLYALKOXYPHENYL)-2-PYRROLIDONES (II)

BACKGROUND OF THE INVENTION

German Patent Application P 24 13 935.3, corresponding to Ralph Schmiechen et al., Ser. No. 560,193, filed Mar. 20, 1975, now U.S. Pat. No. 4,012,495, which is incorporated herein by reference, describes racemic and optically active 4-(polyalkoxyphenyl)-2-pyrrolidones of the formula

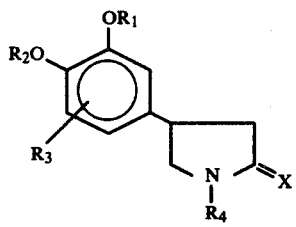

wherein $R_1$ and $R_2$ are identical or different and are hydrocarbon of up to 18 carbon atoms or alkyl of 1-5 carbon atoms substituted by one or more halogen, hydroxy, carboxy, alkoxy, alkoxycarbonyl, carboxamido, or optionally substituted amino, or $R_1$ and $R_2$ collectively are alkylene of 1-3 carbon atoms;

$R_3$ is hydrogen or methoxy;

$R_4$ is hydrogen, alkyl, aryl, or acyl; and

X is oxygen or sulfur, and processes for the preparation thereof.

It has now been found that 4-(polyalkoxyphenyl)-2-pyrrolidones of the above formula wherein $R_4$ is —CO—R and R is O-alkyl, O-aryl, O-aralkyl, $NH_2$—, NH-alkyl, NH-aryl, NH-aralkyl, N(alkyl)$_2$, N(aryl)$_2$, and

have the same pharmacological spectrum of activity, but pronouncedly more protracted effectiveness.

Reference is also made to Ralph Schmiechen et al., Ser. No. 659,082, filed Feb. 18, 1976.

SUMMARY OF THE INVENTION

In a compositional aspect, this invention relates to 4-(polyalkoxyphenyl)-2-pyrrolidones of Formula I

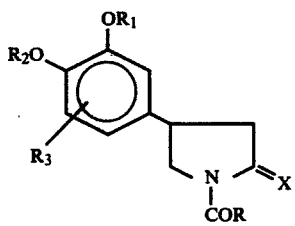

wherein $R_1$ and $R_2$ each are hydrocarbon of up to 18 carbon atoms or alkyl of 1-5 carbon atoms substituted by one or more halogen atoms or by one of hydroxy, carboxy, alkoxy of 1-5 carbon atoms, alkoxycarbonyl of 1-5 carbon atoms in the alkoxy group, carboxamido, alkylcarboxamido, dialkylcarboxamido, carboxcyclicamido, amino, alkylamino, dialkyl or alkyleneimino, wherein alkyl in each instance is of 1-5 carbon atoms and wherein the nitrogen atom of the cyclicamido and alkyleneimino groups is a ring member of alkyleneimino of 4 to 7 members or a morpholino or piperazino ring or $R_1$ and $R_2$ collectively are alkylene of 1-3 carbon atoms;

$R_3$ is hydrogen or methoxy;

R is O-alkyl, O-aryl, O-aralkyl, $NH_2$- , NH-alkyl, NH-aryl, NH-aralkyl, N(alkyl)$_2$, N(aryl)$_2$,

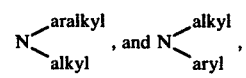

and alkyl is of 1-5 carbon atoms, aryl is aromatic carbocyclic of up to 10 carbon atoms, aralkyl is aromatic carbocyclic of up to 12 carbon atoms in the aromatic ring and 1-4 carbon atoms in the alkyl group;

X is oxygen or sulfur;

and optically active isomers and racemic mixtures thereof.

In another compositional aspect, this invention relates to a pharmaceutical composition for the treatment of neurological and psychic disorders responsive to chlorpromazine therapy, compring a compound of Formula I, in admixture with a pharmaceutically-acceptable carrier.

In a method-of-use aspect, this invention relates to a method of treating neurological and psychic disorders responsive to chlorpromazine therapy and characterized by one or more of the symptoms of anxiety, hostility, agression, withdrawal, hallucination, thought-disturbances, delusions and agitation, which comprises administering to a patient exhibiting the symptoms of such a disorder an amount of a compound of Formula I effective to reduce the symptoms.

In a preparative aspect, this invention relates to preparation of a 4-(polyalkoxyphenyl)-2-pyrrolidone of Formula I by:

(a) saponifying and decarboxylating a 4-(substituted phenyl)-2-pyrrolidone-3-carboxylic acid alkyl ester of Formula II

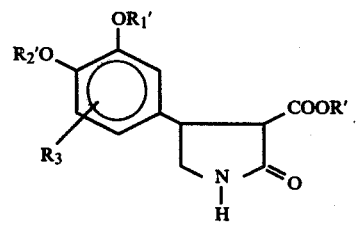

wherein $R_1'$ and $R_2'$ are $R_1$, $R_2$ or hydrogen;

$R_3$ is as above, and

R' is lower alkyl; or (b) cyclizing, by splitting off alcohol, a 3-(substituted phenyl)-4-aminobutyric acid alkyl ester of Formula II

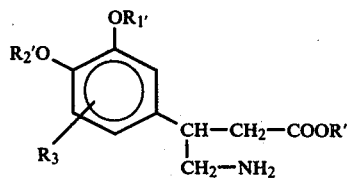

wherein $R_1'$, $R_2'$, $R_3$, and R' are as above, or an acid addition salt thereof; or (c) cyclizing by splitting off water, a 3-(substituted phenyl)-4-aminobutyric acid of Formula IV

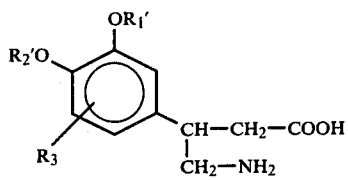

wherein $R_1'$, $R_2'$, and $R_3$ are as above, or an acid addition salt thereof;

and, in a compound obtained according to (a), (b), or (c), acylating an imino (NH);

optionally alkylating or arylating a hydroxy group ($OR_1'$ or $OR_2'$); optionally exchanging a carbonyl oxygen for sulfur and, if a racemate of an optically active compound is formed, subjecting the same to an optional racemate separating step.

DETAILED DESCRIPTION

Compounds of Formula I possess an asymmetrical carbon atom and thus occur as racemates as well as optical antipodes.

Hydrocarbon groups $R_1$ and $R_2$ are saturated and unsaturated, straight-chain and branched alkyl of 1-18 carbon atoms, as well as cycloalkyl and cycloalkylalkyl groups, preferably of 3-7 carbon atoms, and aryl and aralkyl, preferably of 6-10 carbon atoms.

Suitable alkyl groups are, e.g., methyl, ethyl, propyl, isopropyl, butyl, isobutyl, tert.-butyl, pentyl, 2-methylbutyl, 2,2-dimethylpropyl, hexyl, heptyl, octyl, nonyl, 1,2-dimethylheptyl, decyl, undecyl, dodecyl, and stearyl. Alkyl can also be unsaturated, e.g., vinyl, 1-propenyl, 2-propenyl, 2-propynyl, 3-methyl-2-propenyl, etc. Alkyl of 1-5 carbon atoms are preferred.

Alkyl can be mono- or polysubstituted, for example, by halogen, especially fluorine, chlorine, and bromine. Examples of halogen-substituted alkyl are: 2-chloroethyl, 3-chloropropyl, 4-bromobutyl, difluoromethyl, trifluoromethyl, 1,1,2-trifluoro-2-chloroethyl, 3,3,3-trifluoropropyl, 2,2,3,3,3-pentafluoropropyl, 1,1,1,3,3,3-hexafluoro-2-propyl.

Other suitable substituents for alkyl are hydroxy, e.g., 2-hydroxyethyl or 3-hydroxypropyl; carboxy or carbalkoxy of up to 5 carbon atoms in the alkoxy, e.g., carboxymethyl or carboxyethyl; alkoxy, wherein each alkoxy is of 1-5 carbon atoms, e.g., methoxy, ethoxy, propoxy, ethoxymethyl, isopropoxymethyl, 2-methoxyethyl, 2-isopropoxyethyl, 2-butoxyethyl, 2-isobutoxyethyl and 3-pentoxypropyl.

Other substituents on $R_1$ and $R_2$ alkyl are preferably in the ω-position on the chain and include, but are not limited to, alkoxycarbonyl of 1-5 carbon atoms, in the alkoxy, and carboxamido groups wherein nitrogen can be mono- or disubstituted by alkyl groups, preferably of 1-5 carbon atoms, or wherein nitrogen is member of a 4- to 7-membered ring. Examples of alkoxycarbonyl and carboxamido groups are: ethoxycarbonylmethyl, 2-butoxycarbonylethyl, diethylaminocarbonylmethyl, 2-diethylaminocarbonylethyl, 2-pyrrolidinocarbonylethyl, and piperazinocarbonylmethyl, etc. Alkyl of 1-5 carbon atoms can also be terminally substituted by amino wherein the nitrogen can optionally be mono- or disubstituted by alkyl, preferably of 1-4 carbon atoms, or wherein nitrogen is a member of a 4- or 7-membered ring. Examples of N-substituted alkyl groups are: aminomethyl, 2-methylaminoethyl, 2-dimethylaminoethyl, 2-diethylaminoethyl, 3-dimethylaminopropyl, 3-ethylaminopropyl, pyrrolidino, piperidino, N-methylpiperazino, hexamethylenimino, etc.

When $R_1$ and/or $R_2$ in compounds of Formula I are cycloalkyl or cycloalkylalkyl, respectively, they are preferably of 3-7 carbon atoms. Preferred are cyclopropyl, cyclopropylmethyl, cyclopentyl, and cyclohexyl.

Of $R_1$ and/or $R_2$ aryl or aralkyl, phenyl and benzyl are especially preferred, other exemplary aryl and aralkyl include, but are not limited to tolyl, xylyl, mesityl, duryl, ethylphenyl, isopropylphenyl, biphenylyl, benzylphenyl, naphthyl, methylnaphthyl, phenanthryl, benzyl, phenethyl, phenylpropyl and naphthylmethyl.

Compounds of Formula I wherein $R_2$ is methyl are particularly preferred.

In substituents R, alkyl, aryl and aralkyl are hydrocarbons or substituted hydrocarbons as described above, provided that alkyl is of 1-5 carbon atoms, aryl is of up to 10 carbon atoms and aralkyl of up to 12 carbon atoms.

Compounds of this invention include those of Formula I, wherein (a) $R_1$ and $R_2$ each are hydrocarbon of up to 18 carbon atoms;

(a') $R_1$ and $R_2$ each are methyl;

(b) $R_1$ or $R_2$ is alkyl of 1-5 carbon atoms substituted by one or more halogen atoms;

(c) $R_1$ or $R_2$ is alkyl of 1-5 carbon atoms substituted by hydroxy;

(d) $R_1$ or $R_2$ is alkyl of 1-5 carbon atoms substituted by carboxy;

(e) $R_1$ or $R_2$ is alkyl of 1-5 carbon atoms substituted by alkoxy of 1-5 carbon atoms;

(f) $R_1$ or $R_2$ is alkyl of 1-5 carbon atoms substituted by alkoxycarbonyl of 1-5 carbon atoms in the alkoxy;

(g) $R_1$ or $R_2$ is alkyl of 1-5 carbon atoms substituted by carboxamido, alkylcarboxamido, or dialkylcarboxamido and alkyl in each case is of 1-5 carbon atoms;

(h) $R_1$ or $R_2$ is alkyl of 1-5 carbon atoms substituted by carboxycyclicamido and the nitrogen atom of the cyclicamido is a ring member of alkyleneimino of 4 to 7 members, morpholino or piperazino;

(i) $R_1$ or $R_2$ is alkyl of 1-5 carbon atoms substituted by amino, alkylamino or dialkylimino and alkyl is of 1-5 carbon atoms;

(j) $R_1$ or $R_2$ is alkyl of 1-5 carbon atoms substituted by alkyleneimino of 4 to 7 ring members, morpholino or piperazino;

(k) $R_3$ is hydrogen, including (a)–(j);

(l) $R_3$ is methoxy, including (a)–(j);

(m) R is O-alkyl, including (a)–(l);

(n) R is O-aryl or O-aralkyl, including (a)–(l);

(o) R is $NH_2$, NH-alkyl or N(alkyl)$_2$ and alkyl is of 1-5 carbon atoms, including (a)–(l);

(p) R is NH-aryl, NH-aralkyl,

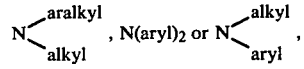

including (a)–(l);

(q) X is oxygen, including (a)–(p); and (r) X is sulfur, including (a)–(p).

Racemic and optically active compounds of Formula I are valuable neuropsychotropic medicaments. The novel compounds show central nervous system (CNS)-depressive, apomorphine-antagonistic, and antinociceptive effects and thus have a certain similarity in activity to chloropromazine. See, "Modern Problems of Pharmacopsychiatry," 5: 33-44, Janssen P.A.Y., "Chemical and Pharmacological Classification of Neuroleptics," edited by Bobon D. P. et al., S. Karger publishers, Basel/Munich/Paris/New York (1970).

Compounds of the invention differ from chloropromazine by virtue of less pronounced impairment of reflexes, less pronounced sedating and narcotic characteristics, and a different effect on biogenic amines. For example, 4-(3,4-dimethoxyphenyl)-2-pyrrolidone exhibits, compared to chloropromazine, a barbital-sleeping period prolonging effect about 20 times weaker.

The novel compounds are characterized by rapid onset of effectiveness and low acute toxicity.

Compounds of this invention substituted on the ring nitrogen by an O- or N-substituted carbonyl group have a markedly protracted effect with the same spectrum of activity.

The properties of the novel compounds are unexpected, since corresponding p- or m-monosubstituted phenyl-2-pyrrolidones have a different spectrum of activity or only a minor activity.

For example, 4-(4-chlorophenyl)-2-pyrrolidone, disclosed in Japanese Patent 70 16 692, has an anticonvulsive effect. Unsubstituted phenyl-2-pyrrolidones have only very weak activity.

The compounds of this invention can be used in the form of pharmaceutical compositions for the treatment of various neurological and psychic disorders, especially as neuroleptics having diminished extrapyramidal symptomatology, for example, schizophrenia and related psychotic states characterized by anxiety, hostility, agression, withdrawal, hallucination, thought-disturbances, delusion and agitation. The compounds of this invention are thus useful for the treatment of such disorders responding to chlorpromazine therapy.

The pharmaceutical compositions of this invention are made with carrier substances customary for enteral or parenteral administration, such as, for example, water, alcohol, gelatin, gum arabic, lactose, amylose, magnesium stearate, talc, vegetable oils, polyalkylene glycol, etc. The preparations can be present in the solid phase as tablets, capsules, dragees, suppositories or in the liquid form as solutions, suspensions, or emulsions.

Although a single racemate or optical antipode of Formula I are generally employed in such compositions, mixtures thereof can also be employed, if desired.

For oral administration, the amount of active agent per oral dosage unit usually is 1-20 mg., preferably 5-10 mg. The daily dosage is usually 1-50 mg., preferably 10-30 mg. p.o. For parenteral application, the amount of active agent per dosage unit is usually 0.05-10 mg., preferably 0.1-5 mg. The daily dosage is usually 0.1-20 mg., preferably 0.2-5 mg. i.v. or i.m.

Conventional methods are utilized to prepare compounds of Formula I.

Saponification by procedure (a) is conducted with aqueous alkali, suitably in a water-miscible solvent, e.g., an alcohol, such as ethanol; tetrahydrofuran, or dioxane; at temperatures between about 60° and 150° C., preferably at the boiling point. Decarboxylation according to (a) takes place by heating a carboxylic acid to about 160°-280° C., preferably under vacuum. Removal of $CO_2$ can optionally also be effected in the presence of a high-boiling inert solvent, for example, in diphenyl ether or quinoline.

Cyclization by method (b) takes place with splitting off of an alcohol in an organic solvent, e.g., dimethylformamide, dimethylacetamide, tetrahydrofuran, dioxane, benzene, toluene, xylene, etc., by heating to about 50°-150° C. If the starting material is a salt, for example, a hydrochloride, of an amino acid ester of Formula III, the heating step is conducted in the presence of a tertiary amine, e.g., a trialkylamine, e.g., triethylamine and tributylamine; N-methylmorpholine, diethylcyclohexylamine, and pyridine.

In process (c), cyclization is conducted while splitting off water at temperatures between about 160° and 280° C. It is advantageous to operate under a vacuum, so that the liberated water can be removed readily and access of atmospheric oxygen prevented. When starting with a corresponding acid addition salt, the heating step is carried out, as for (b), in the presence of a tertiary amine.

Compounds obtained according to (a), (b), or (c), wherein $R_1'$ or $R_2'$ is hydrogen, must subsequently be converted to a final product of Formula I by O-alkylation. The alkylation is preferably conducted in a conventional manner with the corresponding $R_1$ - or $R_2$-halogenide or -tosylate, respectively. Suitable halogenides are chlorides, bromides and iodides. For purposes of alkylation, the hydroxy compound is dissolved, for example, in a polar solvent and heated with the alkylating agent to temperatures between 30° and 150° C. in the presence of a base. Suitable bases are, for example, sodium hydride, potassium carbonate, alkali metal alcoholates, such as sodium ethylate, potassium butylate, and potassium tert.-butylate. Suitable polar solvents are dimethylformamide, dimethylacetamide, tetrahydrofuran, dioxane, ketones, such as acetone and methyl isobutyl ketone, as well as alcohols, such as ethanol, butanol, and tert.-butanol.

The acylation of an imino group likewise is done by conventional methods. Thus, an imino compound ($R_4$ is H) is dissolved in a polar solvent and heated to about 40°-150° C. in the presence of a salt-forming agent with an acyl halogenide. Suitable polar solvents are dimethylformamide; dimethylacetamide; tetrahydrofuran; dioxane; ketones, such as acetone and methyl isobutyl ketone; and alcohols, such as ethanol and butanol. Suitable salt-forming agents are, for example, sodium hydride, potassium carbonate, and alkali metal alcoholates; such as sodium ethylate, potassium tert.-butylate etc.

When conducting the reaction with a halocarbonic acid ester, for example, chlorocarbonic acid alkyl or aryl ester, the solvent can be omitted, and the mixture is heated for a longer period of time at an elevated temperature in the presence of an alkali metal carbonate, such as sodium carbonate.

If an amino compound is reacted with an isocyanate to form a carbamic acid derivative, an inert solvent can be employed, such as halogenated hydrocarbons, e.g., methylene chloride or chloroform.

Exchange of carbonyl oxygen for sulfur is conducted in the same manner as described for such compounds in the literature. See J. W. Scheeren, P. H. J. Ohms, R. J. F. Nivard, Synthesis (1973): 149-151. Suitable for this purpose is, for example, a polysulfide, such as phosphorus pentasulfide in a solvent or solvent mixture and in the presence of a base. The reaction can also be effected in a suspension. Suitable solvents or suspending agents are, e.g., acetonitrile, tetrahydrofuran, diethyl ether, and glycol dimethyl ether. Suitable bases are sodium bicarbonate, potassium carbonate, etc. The reaction is completed after 3-24 hours at 30°-120° C.

Starting compounds of Formulae II, III, and IV can likewise be prepared in accordance with conventional methods, for example as follows:

Starting from a benzaldehyde, substituted by $R_1'$, $R_2'$, $R_3$, a corresponding benzalmalonic acid dialkyl ester is produced by reaction with a malonic acid dialkyl ester.

Substituted benzalmalonic acid dialkyl esters can be converted by reaction with nitromethane in the presence of tetramethylguanidine, to a 1-(substituted phenyl)-2-nitroethylmalonic acid dialkyl ester, which is subsequently hydrogenated under pressure with Raney nickel catalyst, to a 4-(substituted phenyl)-2-pyrrolidone-3-carboxylic acid alkyl ester of Formula II.

To prepare a 3-(substituted phenyl)-4-aminobutyric acid alkyl ester of Formula III, HCN is chemically added to the double bond of a benzalmalonic acid diester using potassium cyanide in aqueous alcohol, and heating to 60° C., during which a carbalkoxy group is simultaneously split off. The cyano compound is hydrogenated under pressure in the presence of platinum dioxide. If HCN addition is conducted under reflux, a corresponding butyric acid of Formula IV is obtained.

The conversion of a substituted benzaldehyde to compounds of Formulae II, III, and IV is summarized by the following reaction scheme:

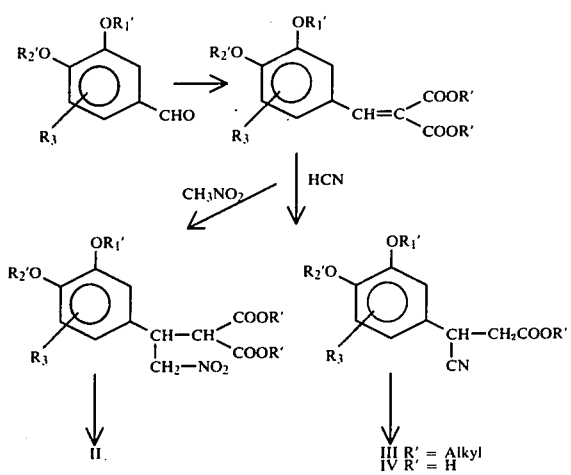

Without further elaboration, it is believed that one skilled in the art can, using the preceding description, utilize the present invention ot its fullest extent. The following preferred specific embodiments are, therefore, to be construed as merely illustrative and not limitative of the remainder of the disclosure in any way whatsoever.

The term "worked up as usual" means extraction with the indicated solvent, washing the organic phase with saturated NaCl solution, drying over anhydrous calcium sulfate, and evaporation under vacuum at a bath temperature of 40°–45° C. Any further treatment of the organic phase, such as washing with acid or an alkaline solution, is described specifically.

The indicated yields are not optimum values. No attempts at optimization have been made.

The temperatures are indicated in each case in degrees Celsium (°C.).

The compounds indicated as being the crude materials were tested for purity by thin-layer chromatography in at least two systems and by IR spectra. All other substances are analytically pure (C-, H-, N-analyses; IR, UV, and NMR spectra; thin-layer chromatography; in some case, titrations and gas chromatography).

Solvents utilized for recrystallization are set forth in parentheses following the melting point, determined on a Kofler heating block.

The following abbreviations are employed for solvents:
DMF: dimethylformamide
EA: ethyl acetate
DIP: diisopropyl ether
W: water
AcOH: glacial acetic acid
Bz: benzene.

Compounds of Formula II can be prepared, for example, as follows:

(A) Benzalmalonic Acid Diethyl Ester

One mole of a correspondingly substituted benzaldehyde is heated with 160 g. of malonic acid diethyl ester (1 mole), 30 ml. of glacial acetic acid, and 3 ml. of piperidine in 1 liter of benzene until one mole of water has been split off and collected in a water trap. The benzene solution is worked up as usual.

3-Isobutoxy-4-methoxybenzaldehyde, not previously described in the literature, is prepared as follows:

108 g. (710 millimoles) of 3-hydroxy-4-methoxybenzaldehyde is heated under agitation for 26 hours at the boiling point with 40.5 g. (723 mmol) of potassium hydroxide and 120 g. (875 mmol) of isobutyl bromide in 250 ml. of ethanol. After the alcohol has been distilled off under vacuum, the residue is worked up as usual with ethyl acetate, but washed additionally with 2N sodium hydroxide solution. By acidification, 35 g. of starting material is recovered from the alkaline extract. The yield of 3-isobutoxy-4-methoxybenzaldehyde is 80 g.; m.p. 70° (heptane).

The following table indicates the yields and the boiling and melting points, respectively, of several compounds.

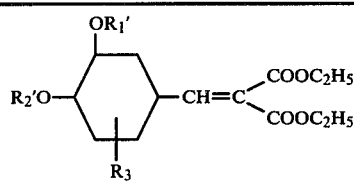

A)

| | $R_1'$ | $R_2'$ | $R_3$ | Yield (% of Theory) | Boiling Point, Melting Point (Recrystallizing Agent) |
|---|---|---|---|---|---|
| a | —CH$_3$ | —CH$_3$ | —H | 70 | bp$_{0.6}$ 185°–189° |

-continued

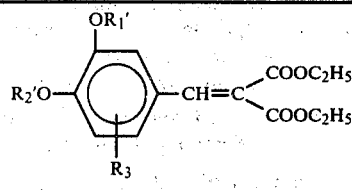

A)

|   | $R_1'$ | $R_2'$ | $R_3$ | Yield (% of Theory) | Boiling Point, Melting Point (Recrystallizing Agent) |
|---|---|---|---|---|---|
| b | —CH$_2$— | | —H | 53 | bp$_{0.4}$ 172° |
| c | —CH$_2$CH$_2$— | | —H | 88 | bp$_1$ 227°–289° |
| d | —CH$_2$CH(CH$_3$)$_2$— | —CH$_3$ | —H | 95 | bp$_{0.1}$ 190°–192° |
| e | —H | —CH$_3$ | —H | 78 | bp$_1$ 213°–215° C. mp. 86° (DIP) |
| f | —CH$_3$ | —H | —H | 77 | mp. 121° (DIP) |
| g | —CH$_3$ | —CH$_3$ | 2-OCH$_3$ | 100 | Crude Product (DC, IR) |
| h | —CH$_3$ | —CH$_3$ | 5-OCH$_3$ | 75 | bp$_{0.2}$ 180°–182° mp. ~ 70° |
| i | —CH$_3$ | —CH$_3$ | 6-OCH$_3$ | 90 | mp. 100° (DIP) |

(B) 1-(Substituted Phenyl)-2-nitroethylmalonic Acid Diethyl Ester 500 millimoles of the corresponding benzalmalonic acid diethyl ester of (A) is dissolved in 250 ml. of nitromethane and combined under agitation at 0° with 12.7 ml. of tetramethylguanidine. After the exothermic reaction has slowed, the mixture is agitated for 18 hours at room temperature. The reaction mixture is worked up as usual with ethyl acetate, but additionally washed with 2N hydrochloric acid. The acetoxymethoxybenzalmalonic acid esters required for Examples B(b) and B(c) are prepared as follows:

150 g. (510 mmol) of the diethyl ester of (3-hydroxy-4-methoxybenzal)-malonic acid of (A)e is dissolved in 450 ml. of pyridine; under ice-cooling, 57 ml. (604 mmol) of acetic anhydride is added dropwise thereto. After allowing the mixture to stand for 18 hours at room temperature, the pyridine is removed under vacuum. The usual work-up operation with ethyl acetate yields 163 g. of the diethyl ester of (3-acetoxy-4-methoxybenzal)-malonic acid (95% of theory); m.p. 75°–77° (diisopropyl ether).

Analogously, the (4-hydroxy-3-methoxybenzal)-malonate of (A) f is acetylated to the corresponding 4-acetoxy-3-methoxy compound. Yield: 95%; m.p. 51° (diisopropyl ether-petroleum ether).

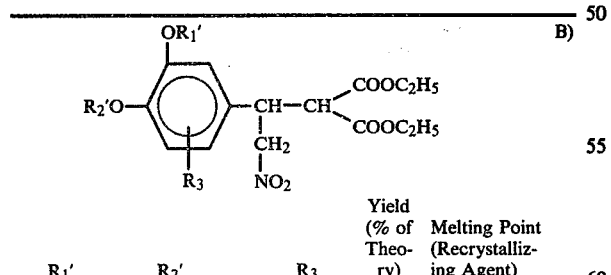

B)

|   | $R_1'$ | $R_2'$ | $R_3$ | Yield (% of Theory) | Melting Point (Recrystallizing Agent) |
|---|---|---|---|---|---|
| a | —CH$_3$ | —CH$_3$ | —H | 59 | 75° (Methylene Chloride-DIP) |
| b | —COCH$_3$ | —CH$_3$ | —H | 95 | Crude Product (TLC, IR) |
| c | —CH$_3$ | —COCH$_3$ | —H | 95 | Crude Product (TLC, IR) |
| d | —CH$_3$ | —CH$_3$ | 2-OCH$_3$ | 65 | Chromatography on SiO$_2$ (Cyclohexane-Ethyl Acetate 1:1) |

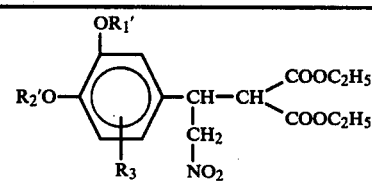

-continued

B)

|   | $R_1'$ | $R_2'$ | $R_3$ | Yield (% of Theory) | Melting Point (Recrystallizing Agent) |
|---|---|---|---|---|---|
| e | —CH$_3$ | —CH$_3$ | 6-OCH$_3$ | 70 | Chromatography on SiO$_2$ (Cyclohexane-Ethyl Acetate 1:1) |

(C) 4-(Substituted Phenyl)-2-pyrrolidone-3-carboxylic Acid Ethyl Ester (II)

300 millimoles of the corresponding 1-phenyl-2-nitroethylmalonic acid diethyl ester is dissolved in 700 ml. of methanol and hydrogenated with about 10 g. of Raney nickel at 60° and under 95 atmospheres of pressure until 3 moles of hydrogen has been absorbed. The mixture is then filtered off from the catalyst, concentrated under vacuum, and the oily residue is recrystallized.

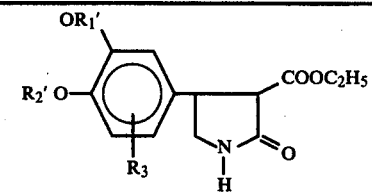

C)

|   | $R_1'$ | $R_2'$ | $R_3$ | Yield (% of Theory) | Melting Point (Recrystallizing Agent) |
|---|---|---|---|---|---|
| a | —CH$_3$ | —CH$_3$ | —H | 84 | 106° (EA) |
| b | —H | —CH$_3$ | —H | 70 | 125° (EA-DIP) (Splitting off the Acetyl Group During Hydrogenation and Working Up) |
| c | —CH$_3$ | —COCH$_3$ | —H | 62 | 172° EA) |
| d | —CH$_3$ | —CH$_3$ | 2-OCH$_3$ | 60 | 99° (EA-DIP) |

-continued

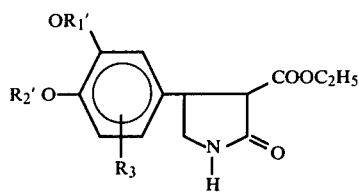

C)

| | $R_1'$ | $R_2'$ | $R_3$ | Yield (% of Theory) | Melting Point (Recrystallizing Agent) |
|---|---|---|---|---|---|
| e | —CH$_3$ | —CH$_3$ | 6-OCH$_3$ | 20 | 131° (Ethanol) | acetate including an extraction with 1N sodium hydroxide solution. Optionally, the corresponding 3-phenyl-3-cyanopropionic acids can be obtained from the sodium hydroxide solution extract by means of acidification.

(E) 3-(Substituted Phenyl)-4-aminobutyric Acid Ethyl Ester Hydrochloride (III)

50 millimoles of a 3-phenyl-3-cyanopropionic acid ethyl ester is hydrogenated in 60 ml. of glacial acetic acid over 1 g. of platinum oxide at room temperature under 100 atmospheres until 2 moles of hydrogen have been absorbed. The mixture is removed from the catalyst by vacuum-filtration and, after adding 25 ml. of 2N methanolic hydrochloric acid, evaporated under vacuum to a small volume.

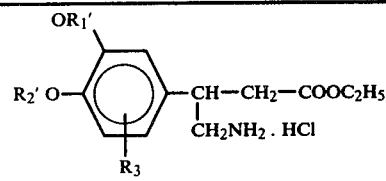

E)

| | $R_1'$ | $R_2'$ | $R_3$ | Yield (% of Theory) | Melting Point (Recrystallizing Agent) |
|---|---|---|---|---|---|
| a | —CH$_3$ | —CH$_3$ | —H | 90 | m.p. 185° (AcOH) |
| b | —CH$_2$— | | —H | 79 | Crude Product (TLC, IR) |
| c | —CH$_2$CH$_2$— | | —H | 100 | Crude Product |
| d | —CH$_2$CH(CH$_3$)$_2$ | —CH$_3$ | —H | 63 | Crude Product (TLC, IR) m.p. 124° (EA) |
| f | —CH$_3$ | —CH$_3$ | 5-OCH$_3$ | 100 | Crude Product (TLC, IR) |
| g | —CH$_3$ | —H | —H | 100 | Crude Product (TLC, IR) |

Compounds of Formula III can be prepared, for example, as follows:

(D) 3-(Substituted Phenyl)-3-cyanopropionic Acid Ethyl Ester 100 millimoles of a corresponding benzalmalonic ester of (A) is combined in 180 ml. of ethanol with a solution of 6.5 g. (100 mmol) of potassium cyanide in 25 ml. of water and heated for 7 hours to 60°. After allowing the reaction mixture to stand for 18 hours at room temperature, the solvents are evaporated under vacuum, and the residue is worked up as usual with ethyl Compounds of Formula IV can be prepared as follows:

(F) 3-(Substituted Phenyl)-3-cyanopropionic Acid

By the reaction of a correspondingly substituted benzalmalonic ester of (A) with potassium cyanide in the same quantitative ratios and within the same reaction times as described under (D), but under reflux, the 3-(substituted phenyl)-3-cyanopropionic acids are obtained. These compounds are isolated, after evaporation

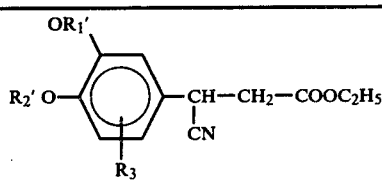

D)

| | $R_1'$ | $R_2'$ | $R_3$ | Yield | Boiling Point Melting Point (Recryst. Agent) |
|---|---|---|---|---|---|
| a | —CH$_3$ | —CH$_3$ | —H | 85 | bp$_{0.1}$ 177-182° |
| b | —CH$_2$— | | —H | 82 | Crude Product (TLC, IR) |
| c | —CH$_2$CH$_2$— | | —H | 84 | Crude Product (TLC, IR) |
| d | —CH$_2$CH(CH$_3$)$_2$ | —CH$_3$ | —H | 83 | Crude Product |
| e | —CH$_3$ | —H | —H | 91 | (TLC, IR) |
| f | —CH$_3$ | —CH$_3$ | 5-OCH$_3$ | 60 | Crude Product (TLC, IR) m.p. 84° (EtOH) | of the solvents, by taking up the reside in water, washing with ethyl acetate, and acidifying the aqueous phase and purified by crystallization.

thoxyphenyl)-2-pyrrolidone-1-carboxylic acid, m.p. 86°-87° (ethyl acetate/petroleum ether).

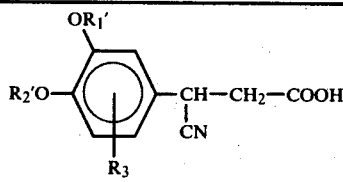

F)

| | $R_1'$ | $R_2'$ | $R_3$ | Yield (% of Theory) | Melting Point (Recrystallizing Agent) |
|---|---|---|---|---|---|
| a | —$CH_3$ | —$CH_3$ | —H | 54 | m.p. 133°–135° (Ethano |
| b | | —$CH_2$— | —H | 63 | Crude Product (TLC, IR) |
| c | | —$CH_2CH_2$— | —H | 76 | Crude Product (TLC, IR) |
| d | —$CH_3$ | —$CH_3$ | 5-$OCH_3$ | 78 | Crude Product (TLC, IR) |

(G) 3-(Substituted Phenyl)-4-aminobutyric Acid Hydrochloride (IV)

100 millimoles of 3-(substituted phenyl)-3-cyanopropionic acid of (F) is hydrogenated in 200 ml. of glacial acetic acid with the addition of 9.5 ml. of concentrated hydrochloric acid over 3 g. of platinum dioxide at room temperature and under 100 atmospheres until 2 moles of hydrogen has been absorbed. The mixture is filtered off from the catalyst and evaporated under vacuum. By crystallization of the mostly oily residue, the 3-(substituted phenyl)-4-aminobutyric acid hydrochlorides are obtained.

EXAMPLE 3

0.221 g. of 4-(3,4-dimethoxyphenyl)-2-pyrrolidone is combined in 10 ml. of methylene chloride with 3 ml. of chlorosulfonyl isocyanate and agitated for 1.5 hours at room temperature. The charge is worked up as usual with methylene chloride and purified by column chromatography on silica gel with chloroform/acetate (1:1), thus obtaining 0.026 g. of 4-(3,4-dimethoxyphenyl)-2-pyrrolidone-1-carboxylic acid amide, m.p. 125°–127° (methanol).

EXAMPLE 4

4-(3,4-Dimethoxyphenyl)-2-pyrrolidone-1-carboxylic

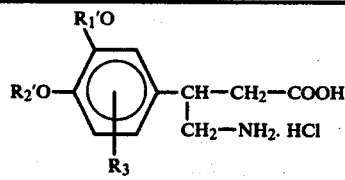

G)

| | $R_1'$ | $R_2'$ | $R_3$ | Yield (% of Theory) | Melting Point (Recrystallizing Agent) |
|---|---|---|---|---|---|
| a | —$CH_3$ | —$CH_3$ | —H | 50 | m.p. 220° (decomp.) (AcOH) |
| b | | —$CH_2$— | —H | 43 | m.p. 210° (1N HCl) |
| c | | —$CH_2CH_2$— | —H | 52 | m.p. 207° (Ethanol-DIP) |
| d | —$CH_3$ | —$CH_3$ | 5-$OCH_3$ | 45 | m.p. 204° (Isopropanol) |

EXAMPLE 1

2.21 g. (10 mmol) of 4-(3,4-dimethoxyphenyl)-2-pyrrolidone is agitated with 1 g. of anhydrous sodium carbonate and 30 ml. of the ethyl ester of chlorocarbonic acid for 16 hours at 100°, then filtered, and evaporated under vacuum, thus obtaining 1.09 g. of the ethyl ester of 4-(3,4-dimethoxyphenyl)-2-pyrrolidone-1-carboxylic acid, m.p. 88°–90° (ethyl acetate/petroleum ether).

EXAMPLE 2

2.21 g. of 4-(3,4-dimethoxyphenyl)-2-pyrrolidone is reacted analogously to Example 1 with the benzyl ester of chlorocarbonic acid; the product is purified by chromatography on silica gel with benzene/ethyl acetate (1:1). Yield: 1.24 g. of the benzyl ester of 4-(3,4-dime- Acid Amides 2.21 g. of 4-(3,4-dimethoxyphenyl)-2-pyrrolidone is heated to boiling with an isocyanate of the general formula R-NCO in about a ten-fold excess for 2.5 hours and thereafter evaporated under vacuum.

Depending on the isocyanate employed, the following 1-carboxylic acid amides are obtained:

| R | Yield | Melting Point (Recrystallizing Agent) |
|---|---|---|
| —$CH_3$ | 1.47 g. | 95°–98° (EA-DIP) |
| —CH(CH$_3$)$_2$ | 1.53 g. | 105°–107° (EA-Petroleum Ether) |

| R | Yield | Melting Point (Recrystallizing Agent) |
|---|---|---|
|  | 2.62 g. | 110°–112° (EA-Petroleum Ether) |

EXAMPLE 5

2.78 g. (10 mmol) of 4-(3,4-dimethoxyphenyl)-2-pyrrolidone-1-carboxylic acid methylamide is combined in 20 ml. of dimethylformamide at 0° under agitation with 0.5 g. of sodium hydride (50% strength). After the evolution of hydrogen has ceased, 1.27 g. of benzyl chloride is added dropwise to the reaction mixture and the latter is stirred for 16 hours at room temperature. The solvent is evaporated under vacuum and worked up as usual with ethyl acetate, thus obtaining 1.58 g. of 4-(3,4-dimethoxyphenyl)-2-pyrrolidone-1-carboxylic acid N-benzyl-N-methylamide, m.p. 76°–78°, (EA-DIP).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 4-(polyalkoxyphenyl)-2-pyrrolidone of the formula

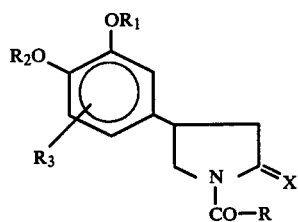

wherein $R_1$ and $R_2$ each are hydrocarbon of up to 18 carbon atoms or $C_{1-5}$ alkyl, $C_{2-5}$ alkenyl or $C_{2-5}$ alkynyl each substituted by a halogen atom or by one of hydroxy, carboxy, alkoxy of 1–5 carbon atoms, alkoxycarbonyl of 1–5 carbon atoms in the alkoxy group, carboxamide, alkylcarboxamide, dialkylcarboxamido, amino, alkylamino or dialkyl, wherein alkyl in each instance is of 1–5 carbon atoms or $R_1$ and $R_2$ collectively are alkylene of 1–3 carbon atoms;

$R_3$ is hydrogen or methoxy;

R is O-aliphatic, O-aryl, O-aralkyl, $NH_2$-, NH-aliphatic, NH-aryl, NH-aralkyl, N(aliphatic)$_2$,

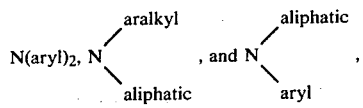

and "aliphatic" is $C_{1-5}$ alkyl, $C_{2-5}$ alkenyl or $C_{2-5}$ alkynyl, aryl is phenyl, $C_{1-4}$ alkylphenyl, naphthyl or biphenyl, and aralkyl is aromatic carbocyclic of up to 12 carbon atoms in the aromatic ring and 1–4 carbon atoms in the alkyl group;

X is oxygen or sulfur;

and optically active isomers and racemic mixtures thereof.

2. A compound of claim 1, wherein X is oxygen.
3. A compound of claim 2, wherein $R_3$ is H.
4. A compound of claim 3, wherein $R_1$ and $R_2$ each are methyl.
5. A compound of claim 4, wherein R is O-alkyl.
6. A compound of claim 4, wherein R is O-aryl or O-aralkyl.
7. A compound of claim 4, wherein R is $NH_2$, NH-alkyl or N(alkyl)$_2$ and alkyl is of 1–5 carbon atoms.
8. A compound of claim 4, wherein R is NH-aryl, NH-aralkyl, N(aryl)$_2$ or

9. Ethyl ester of 4-(3,4-dimethoxyphenyl)-2-pyrrolidone-1-carboxylic acid, a compound of claim 1.
10. Benzyl ester of 4-(3,4-dimethoxyphenyl)-2-pyrrolidone-1-carboxylic acid, a compound of claim 1.
11. 4-(3,4-Dimethoxyphenyl)-2-pyrrolidone-1-carboxylic acid amide, a compound of claim 1.
12. 4-(3,4-Dimethoxyphenyl)-2-pyrrolidone-1-carboxylic acid methylamide, a compound of claim 1.
13. 4-(3,4-Dimethoxyphenyl)-2-pyrrolidone-1-carboxylic acid isopropylamide, a compound of claim 1.
14. 4-(3,4-Dimethoxyphenyl)-2-pyrrolidone-1-carboxylic acid phenylamide, a compound of claim 1.
15. 4-(3,4-Dimethoxyphenyl)-2-pyrrolidone-1-carboxylic acid N-benzyl-N-methylamide, a compound of claim 1.
16. A pharmaceutical composition for the treatment of neurological and psychic disorders responsive to chlorpromazine therapy, comprising an amount of a compound of claim 1 effective to treat the disorders, in admixture with a pharmaceutically-acceptable carrier.
17. A method of treating neurological and psychic disorders responsive to chlorpromazine therapy and characterized by one or more of the symptoms of anxiety, hostility, agreesion, withdrawal, hallucinations, thought-disturbances, delusions and agitation, which comprises administering to a patient exhibiting the symptoms of such a disorder an amount of a compound of claim 1 effective to reduce the symptoms.

* * * * *